United States Patent [19]

LaMont

[11] Plant 4,800

[45] Jan. 19, 1982

[54] COMPACT CORTLAND APPLE TREE—LAMONT CULTIVAR

[75] Inventor: George LaMont, Albion, N.Y.

[73] Assignee: Stark Brothers Nurseries & Orchards Company, Louisiana, Mo.

[21] Appl. No.: 141,974

[22] Filed: Apr. 21, 1980

[51] Int. Cl.[3] ..... A01H 5/00

[52] U.S. Cl. ..... Plt./34

[58] Field of Search ..... Plt./34

*Primary Examiner*—James R. Feyrer

*Attorney, Agent, or Firm*—Burns, Doane, Swecker & Mathis

[57] ABSTRACT

A new and distinct apple variety which originated as a limb mutation of the standard Cortland apple tree (non-patented) is provided. This new apple variety can be distinguished by its compact vigorous growth habit, and the ability to form fruit on spurs which are present in substantially greater numbers per linear foot on two, three, and four year old wood. The tree upon maturity is only approximately 60 to 65 percent of the size of the standard Cortland apple tree.

2 Drawing Figures

SUMMARY OF THE INVENTION

The new and distinct variety of apple tree was discovered by me in 1970 while growing as a limb mutation in my cultivated orchard containing standard Cortland apple trees (non-patented) located on Peter Smith Road in Kendall Township, Orleans County, N.Y. I was attracted to the new variety by its compact spur-type growth habit whereby fruiting spurs were borne surprisingly heavily on two, three, and four year old wood.

The new variety possesses substantially shorter internodes or spacing between leaves on one year old twigs, and the fruiting spurs are substantially more numerous per linear foot than on the standard Cortland variety. Little blindwood and dead spur is found on three and four year old wood.

The new variety exhibits substantial vigor and possesses a more upright growth habit with only a slightly spreading tendency. For instance, branches of the present variety tend to form an angle of approximately 45° to 60° in relation to the leader, while branches of the standard Cortland variety tend to form an angle of approximately 60° to 75° in relation to the leader. Because of its only slightly spreading tendency the new variety has the ability to better sustain heavy crops without limb breakage caused by the weight of the fruit crop. When grown on Malling IX rootstock the new variety possesses only approximately 60 to 65 percent of the tree canopy volume as the standard Cortland variety also on Malling IX rootstock.

The fruit of the new variety is substantially identical to that of the standard Cortland variety in shape, appearance, texture, etc. Fruit production begins at an early age if good horticultural practices are followed. The stem of the new variety is somewhat stouter than that of the standard Cortland variety.

Asexual propagation by budding on Malling IX rootstock beginning in 1972 at Wolcott, N.Y. has demonstrated that the unique combination of characteristics of this new variety comes true to form and is established and transmitted through succeeding propagations.

The specimens described herein were grown at Kendall Township, Orleans County, N.Y.

The new variety has been named the LaMont cultivar.

BRIEF DESCRIPTION OF THE PHOTOGRAPHS

FIG. 1 shows typical specimens of the fruit and foliage on two and three year old wood of the new variety in color as nearly true as it is reasonably possible to make the same in a color illustration of this character.

FIG. 2 shows for comparative purposes typical two and three year old branches without foliage (i.e. foliage has been removed) of the standard Cortland apple tree and of the LaMont cultivar apple tree in color as nearly true as it is reasonably possible to make the same in a color illustration of this character. Note the lack of spur formation on the upper branch of the standard Cortland, and the heavy spur formation on the lower branch of the LaMont cultivar.

DETAILED DESCRIPTION OF THE NEW VARIETY

Figure 1:
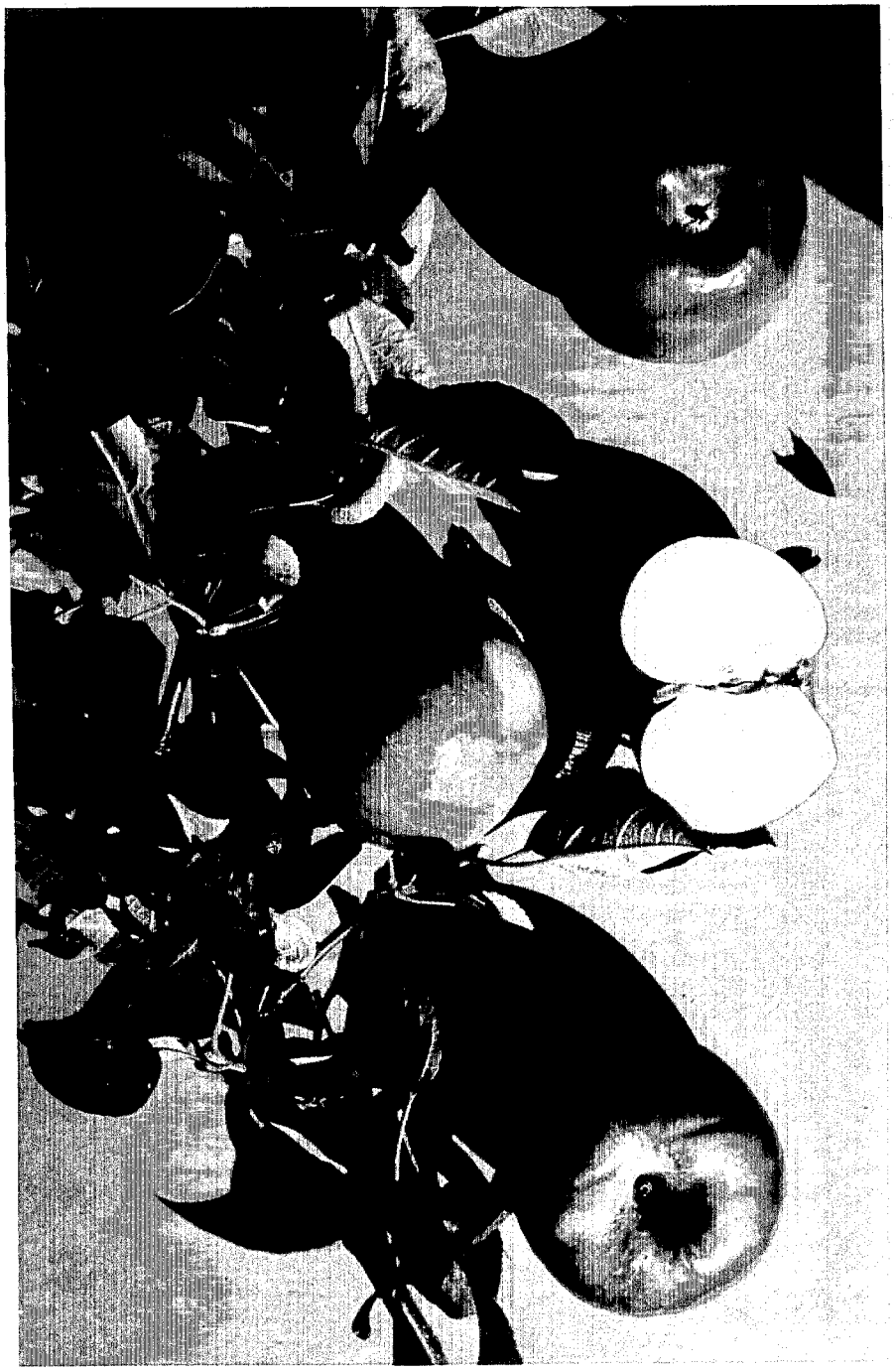
Figure 2:
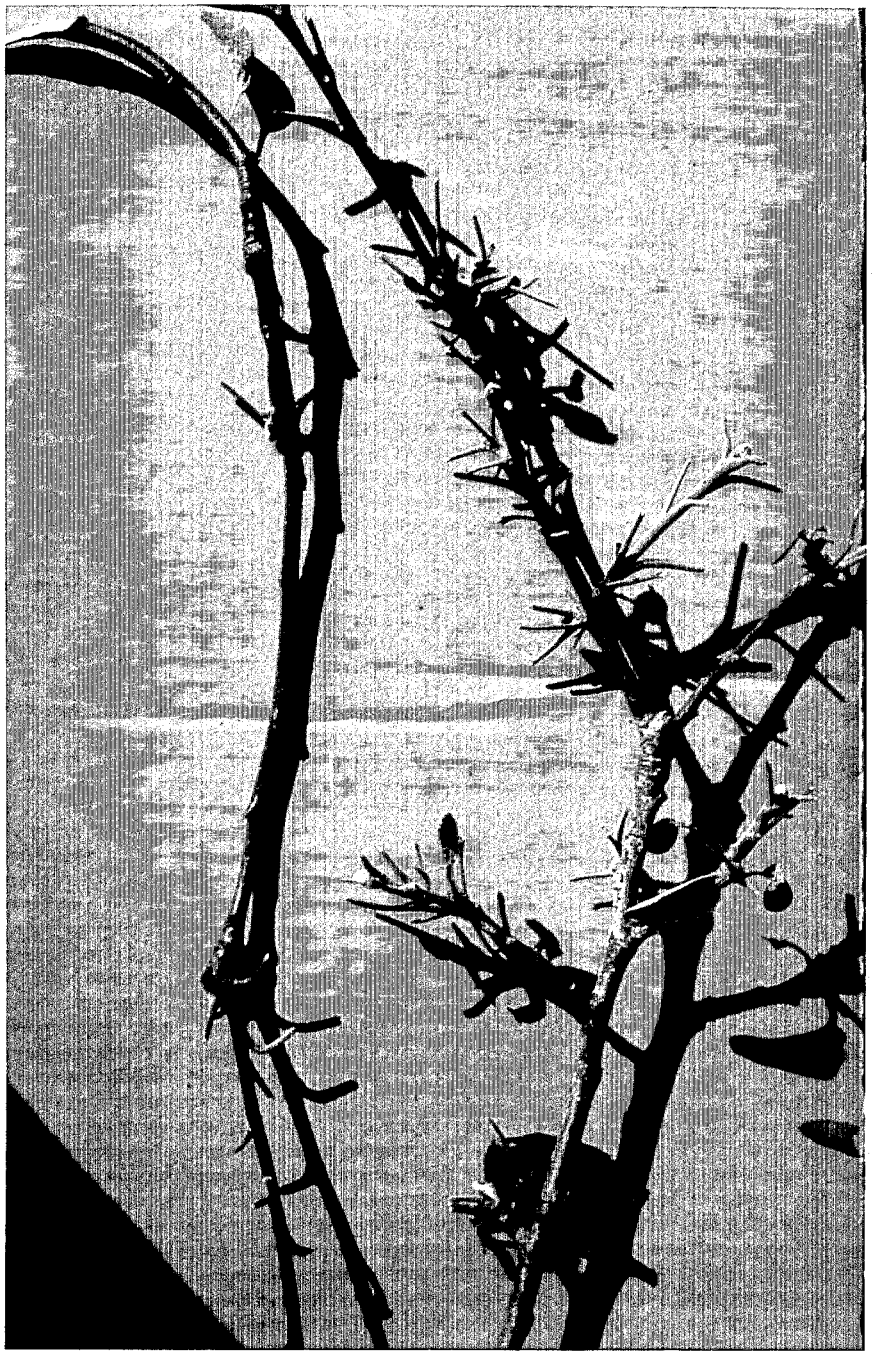

Dates of first and last pickings: Substantially the same as the standard Cortland variety; the fruit commonly is ripe about October 1 to October 10 in New York depending upon the specific growing conditions encountered.

Tree: Medium; medium weak; upright to spreading; dense; vase-formed; hardy; very productive; regular bearing.

*Trunk.*—Stocky; uncommonly smooth.

*Branches.*—Thick; smooth; much spur branching; gray.

*Leaves.*—Large; wide; medium; abruptly pointed; medium thick; medium green; rugose. Length — approximately 3½ inches. Width — approximately 2-9/16 inches. Margin — glandular; coarsely serrate. Petiole — approximately 1⅛ inches; short; thick.

Flowers

*Date of first bloom.*—May 9, 1979.

*Date of full bloom.*—May 16, 1979. Medium early; large; white with pink center.

Fruit

*Maturity.*—When eating ripe, approximately October 10.

*Size.*—Uniform; axial diameter approximately 3½ inches; roundish oblate; ribbed.

*Cavity.*—Abrupt at base; obtuse. Depth — approximately ½ inch. Breadth — approximately 1½ inches. Markings — none.

*Basin.*—Depth. — approximately ⅝ inch. Breadth — approximately 1¼ inches. Markings — none.

*Stem.*—Stout; pubescent. Length — short; approximately ⅜ inch. Breadth — approximately ⅛ inch. Markings — none.

*Calyx.*—Open; obtuse. Length — approximately 9 mm. Outer surface — glabrous. Inner surface — glabrous.

*Eye.*—Partially closed.

*Skin.*—Thick; tough; smooth; glossy. Dots — obscure; few; small; depressed. Color of dots — light brown. Distribution of dots — uniform; few. Ground color — approximately 10 percent. Color markings — approximately 90 percent; splashed; bright. Color of markings — very dark; Ridgeway Color Standards and Nomenclature 1-i Carmine. Bloom — abundant. General color effect — dark red; Carmine.

*Flesh.*—Texture — semi-firm; tender firm; fine; crisp. Flavor — subacid. Aroma — aromatic. Quality — very good.

*Core.*—Medium; broadly ovate; symmetrical at base; opposite with cell. Halves of area — unequal. Bundles — conspicuous; in one whorl. Alternate bundle — approximate to distant. Core lines — meeting; indistinct. Carpellary area — distinct. Calyx tube — glabrous toward base; stem of funnel short. Depth of tube to shoulder — approximately ⅛ inch. Entire depth — approximately ⅜ inch. Styles — present; united. Stamens — two obscure, whorls median. Auxillary cavity — wanting. Seed cells axile — open to closed. Breadth — approximately 7/16 inch. Longitudinal section — broadly ovate; obtuse at apex. Surface — entire, smooth. Cross section — broad.

*Seeds.*—Number perfect — 5 to 8; imperfect — 0 to 3. Number in one cell — 3. Length — approximately ¼ inch. Breadth — approximately 3/16 inch. Form — acute. Color — brown to light brown.

Use: Dessert, culinary.

Keeping quality: Medium.

*Number of days in ordinary storage.*—90 to 120 days.

I claim:

1. A new and distinct variety of apple tree which is a limb mutation of the standard Cortland apple tree (nonpatented), substantially as shown and described, characterized by a compact vigorous growth habit, and the ability to bear fruit on spurs produced in greater numbers per linear foot on two, three, and four year old wood.

* * * * *

Standard Cortland

Compact Cortland
LaMont Cultivar